(12) United States Patent
Green

(10) Patent No.: US 7,278,563 B1
(45) Date of Patent: Oct. 9, 2007

(54) SURGICAL INSTRUMENT FOR PROGRESSIVELY STAPLING AND INCISING TISSUE

(76) Inventor: David T. Green, 40 Madison Hill, Fairfield, CT (US) 06430

( * ) Notice: Subject to any disclaimer, the term of this patent is extended or adjusted under 35 U.S.C. 154(b) by 43 days.

(21) Appl. No.: 11/410,346

(22) Filed: Apr. 25, 2006

(51) Int. Cl.
*A61B 17/068* (2006.01)

(52) U.S. Cl. .................. 227/180.1; 227/19; 227/176.1

(58) Field of Classification Search ............ 227/176.1, 227/178.1, 180.1, 175.1, 19
See application file for complete search history.

(56) References Cited

U.S. PATENT DOCUMENTS

| | | | |
|---|---|---|---|
| 3,499,591 | A | 3/1970 | Green |
| 5,485,952 | A | 1/1996 | Fontayne |
| 5,560,532 | A | 10/1996 | DeFonzo et al. |
| 5,632,432 | A * | 5/1997 | Schulze et al. ........... 227/176.1 |
| 5,667,517 | A * | 9/1997 | Hooven ....................... 606/151 |
| 5,690,269 | A | 11/1997 | Bolanos et al. |
| 5,901,895 | A | 5/1999 | Heaton et al. |
| 5,954,259 | A * | 9/1999 | Viola et al. ............... 227/176.1 |
| 5,993,464 | A | 11/1999 | Knodel |
| 6,010,054 | A * | 1/2000 | Johnson et al. ........... 227/176.1 |
| 6,179,195 | B1 * | 1/2001 | Adams et al. ............ 227/180.1 |
| 6,460,749 | B1 | 10/2002 | Levinson et al. |
| 6,578,751 | B2 * | 6/2003 | Hartwick .................. 227/176.1 |
| 6,716,232 | B1 * | 4/2004 | Vidal et al. ................. 606/205 |
| 7,140,527 | B2 * | 11/2006 | Ehrenfels et al. ........ 227/175.1 |
| 7,159,750 | B2 * | 1/2007 | Racenet et al. .......... 227/180.1 |

\* cited by examiner

*Primary Examiner*—Scott A. Smith
(74) *Attorney, Agent, or Firm*—Scott D. Wofsy; George N. Chaclas; Edwards Angell Palmer & Dodge, LLP

(57) ABSTRACT

An instrument including a clamping jaw with an anvil defining an elongated slot and staple forming cups on opposing sides of the elongated slot. A housing rotatably mounts on the anvil and a pusher rotatably mounts within the housing. A handle actuates the clamping jaw from the open to the intermediate position by rotating the housing towards the clamping jaw. To move from the intermediate position to the closed position, the pusher rotates towards the anvil. A staple cartridge, disposed in the housing, includes a staple track for retaining two rows of staples on opposing sides of the elongated slot. Two staple drivers align with the distal most staples. The drivers slidably mount in the staple cartridge and couple to the pusher such that each staple driver forces a staple into the forming cups and, in turn, staples the body tissue as the pusher rotates from the intermediate to closed position. A knife rotatably mounts on the staple cartridge and couples to the pusher such that the knife passes into the elongated slot and, in turn, cuts the body tissue as the pusher rotates from the intermediate to closed position.

27 Claims, 12 Drawing Sheets

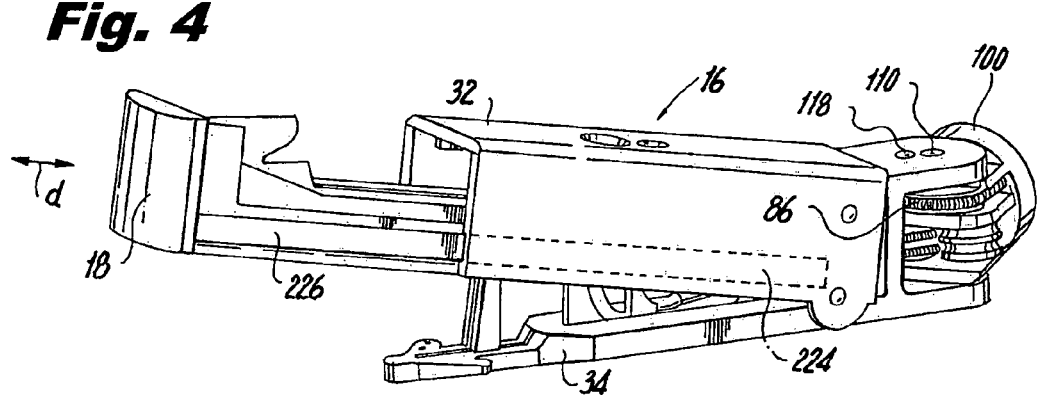
Fig. 4
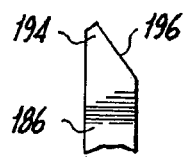
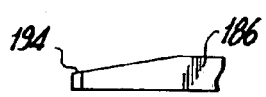
Fig. 9
Fig. 10
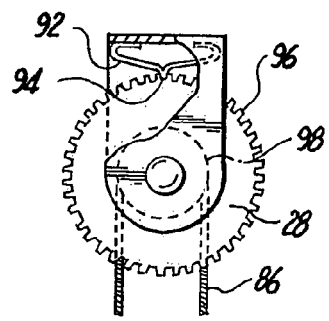
Fig. 5
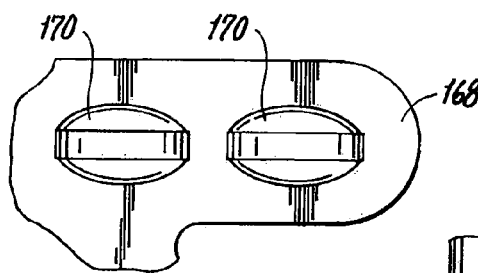
Fig. 11
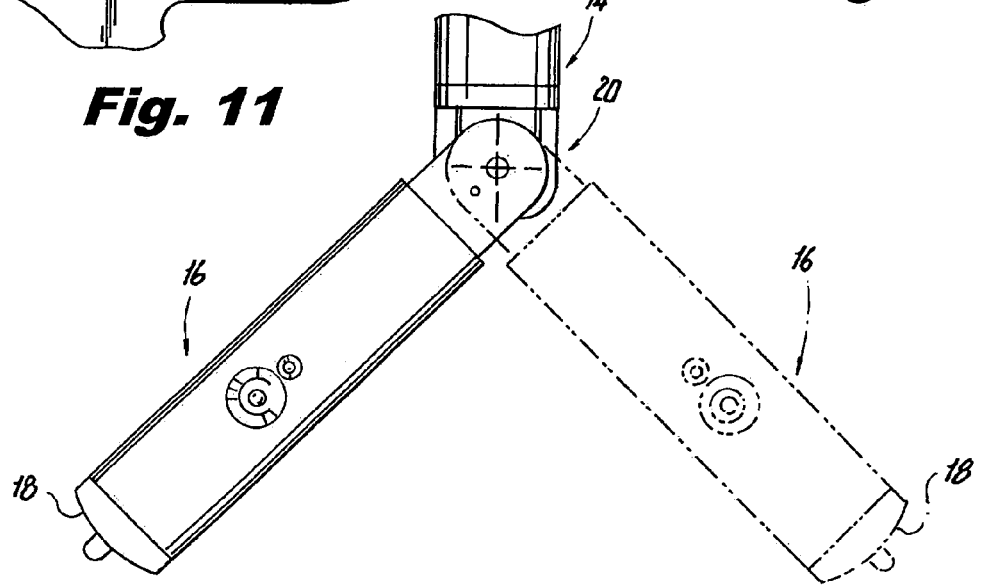
Fig. 6

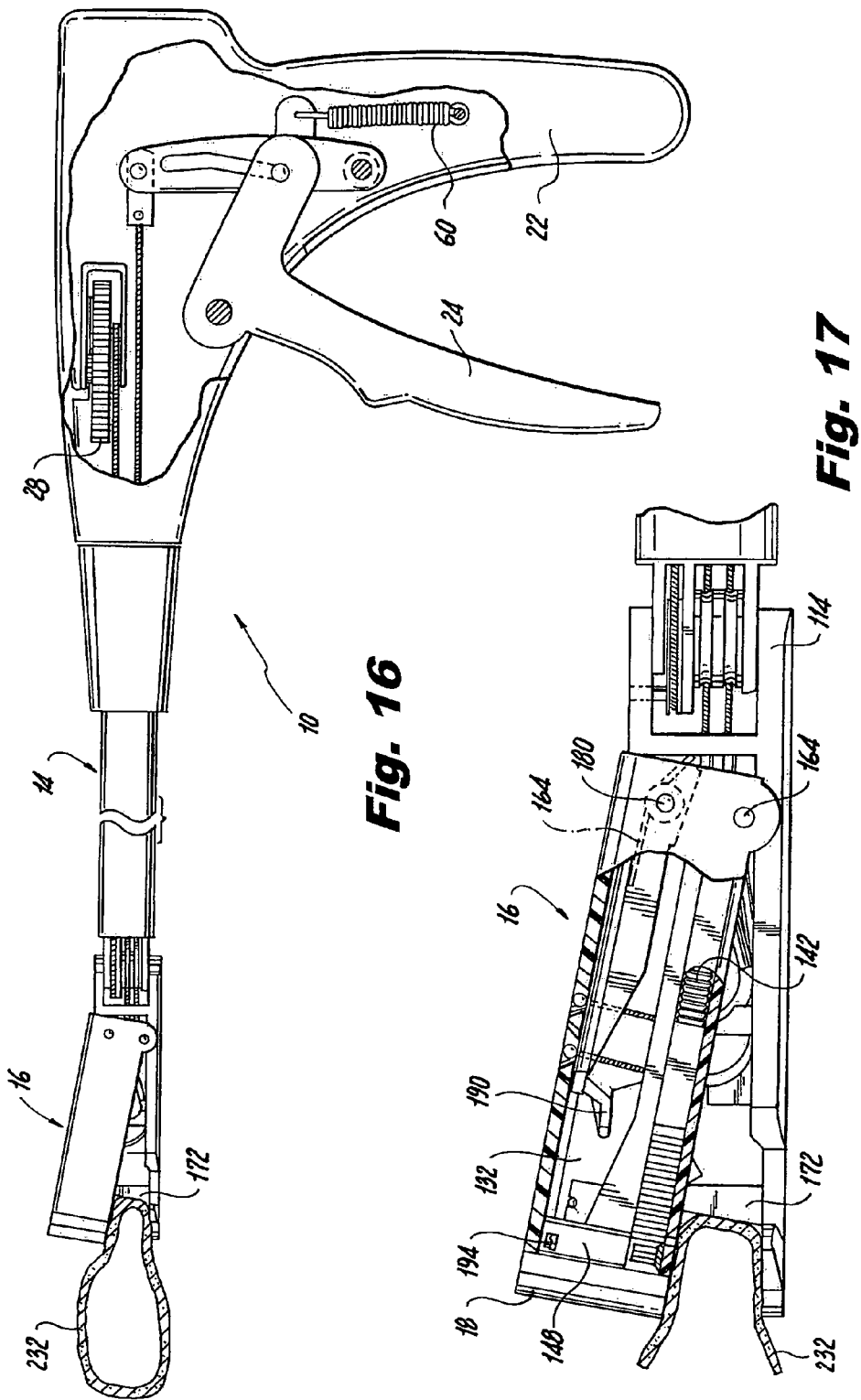

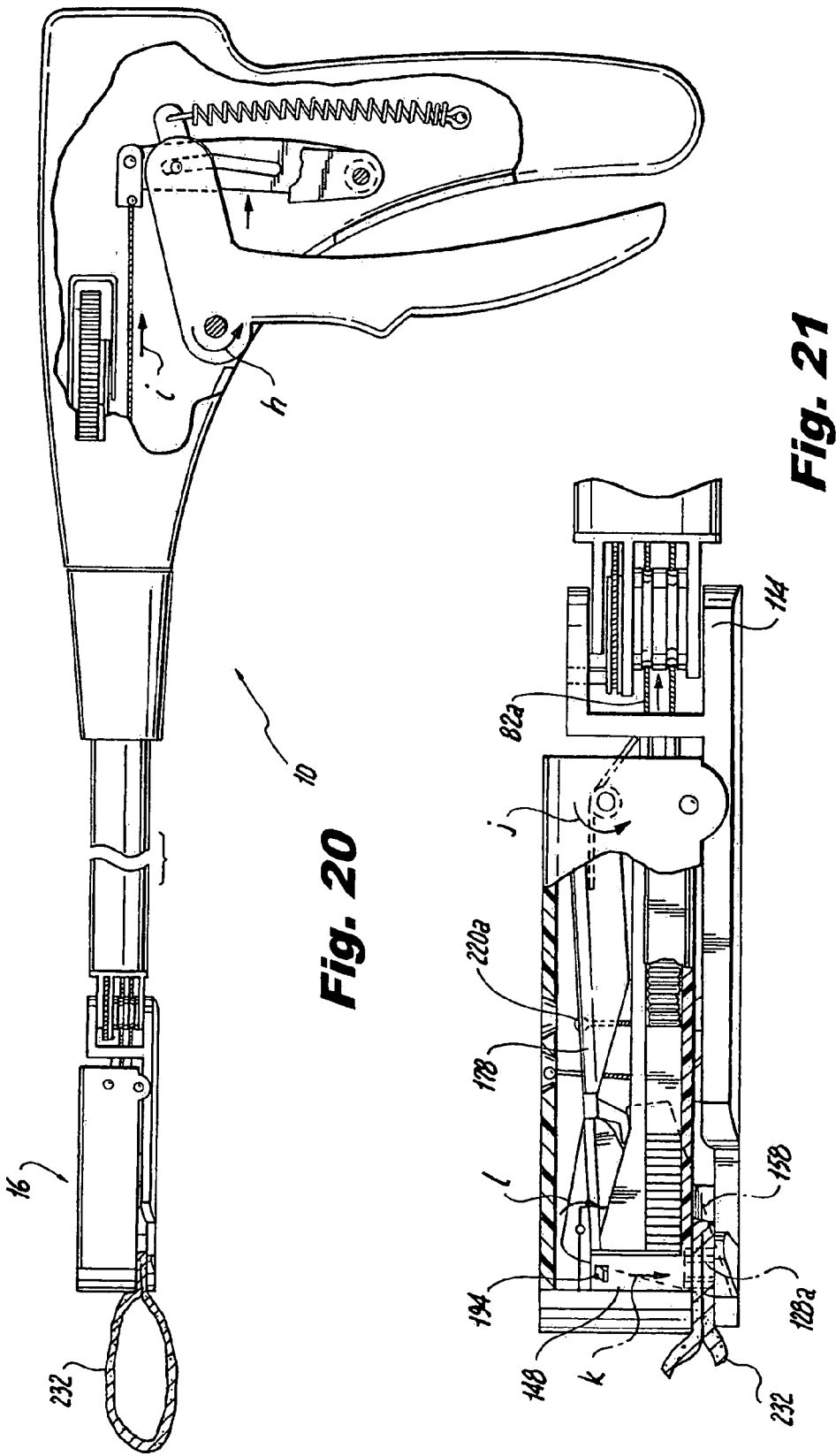

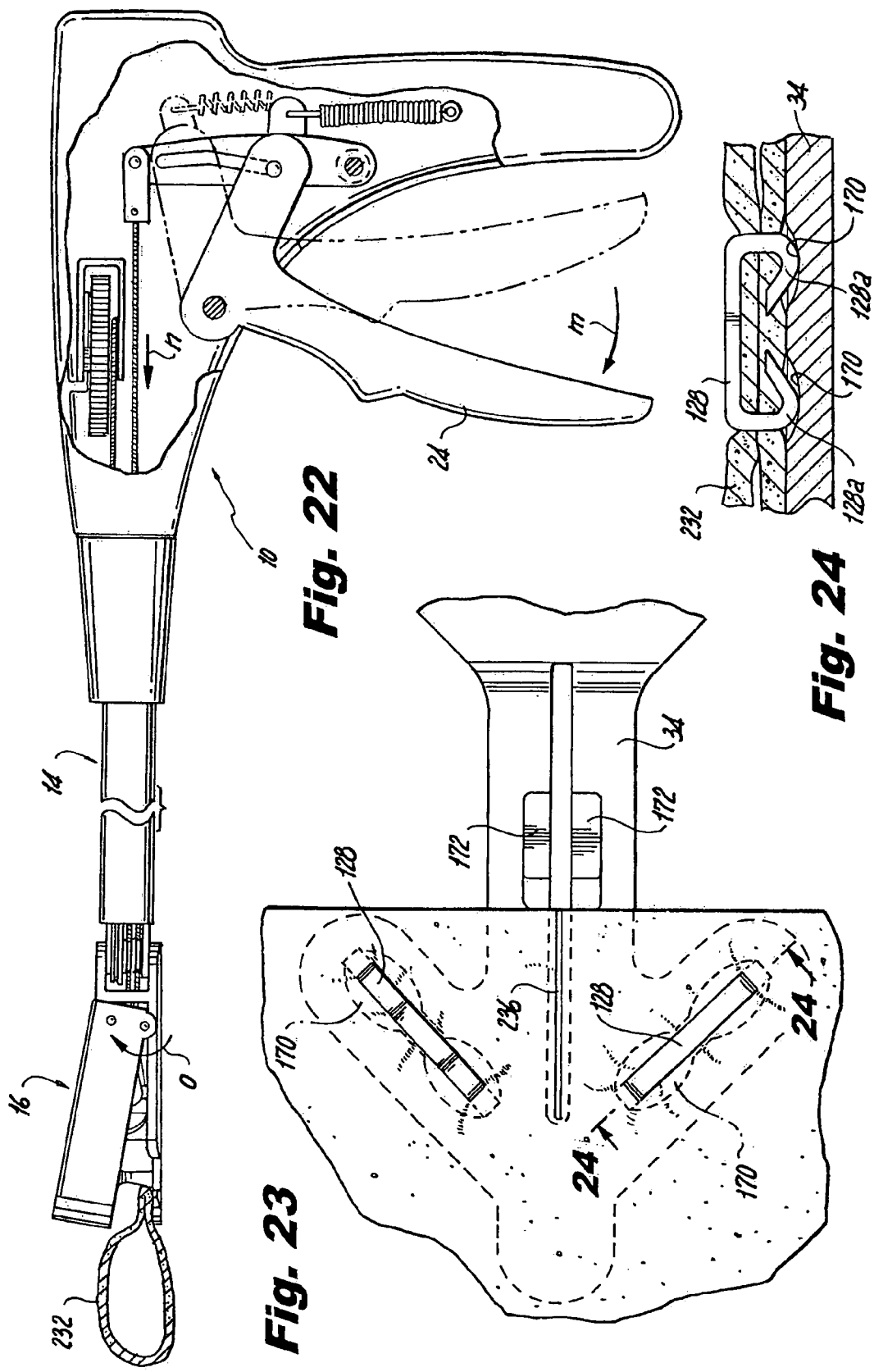

SURGICAL INSTRUMENT FOR PROGRESSIVELY STAPLING AND INCISING TISSUE

BACKGROUND OF THE INVENTION

1. Field of the Invention

The subject disclosure relates to surgical instruments and methods for cutting and applying surgical staples to body tissue, and more particularly, to a surgical instrument for progressively forming an incision in body tissue while placing staples on each side of the incision.

2. Background of the Related Art

Many surgical procedures often require the application of one or more surgical fasteners to body organs and tissue. In many instances, the fasteners used are unitary metal staples. Such metal staples are used in numerous types of surgical procedures. In most surgical procedures, the staples are applied directly to the body tissue requiring attachment, reattachment, ligation, etc. In certain other procedures, staples are used to attach an intermediate object to the body tissue. In still other procedures, cutting of the body tissue in areas adjacent the stapling is also desired.

In view of the above, surgical stapling instruments are known wherein tissue is first grasped or clamped between opposing jaw structure and then fastened by means of fasteners. In some instruments, a knife is provided to cut tissue which has been joined by the fasteners. Instruments for this purpose can include two elongated jaws which are respectively used to capture or clamp tissue. Typically, one of the jaws carries a disposable cartridge wherein a plurality of staples are arranged in a row while the other jaw has an anvil for forming the staple legs as the staples are driven from the cartridge. Generally, the stapling operation is effected by a camming element which travels longitudinally through the cartridge and acts upon individual staple pushers to sequentially eject the staples from the cartridge. A knife can be positioned in such a manner so as to operate sequentially immediately behind the camming element and laterally positioned between the staple rows to longitudinally cut and/or open the stapled tissue. Such instruments are disclosed, for example, U.S. Pat. No. 3,490,675 to Green and U.S. Pat. No. 5,901,895 to Green.

An instrument disclosed in U.S. Pat. No. 3,499,591 to Green applies a double row of staples on each side of the incision. This is accomplished by a cartridge assembly wherein a cam member moves within an elongate guide path between two sets of staggered staple carrying grooves. Staple drive members are positioned in such a manner so as to be contacted by the longitudinally moving cam to effect ejection of the staples. The cartridge assemblies typically come in a plurality of sizes, each varying in both length and number of staples contained therein. Depending on the procedure to be performed, the surgeon must select the appropriate cartridge assembly.

The instruments described above were all designed for use in surgical procedures wherein surgeons have direct access to the operation site. However, in endoscopic or laparoscopic procedures, surgery is performed through a small incision or through narrow cannulae inserted through entrance wounds in the skin. In order to address the specific needs of endoscopic and/or laparoscopic surgical procedures, endoscopic surgical stapling devices such as those disclosed in U.S. Pat. No. 5,040,715 and U.S. Pat. No. 5,318,221, both to Green et al., have been developed. In general, these instruments are provided with clamping structure to effect approximation of an anvil and a staple cartridge to secure tissue therebetween, and staple firing structure to effect sequential ejection of a plurality of staples from the staple cartridge after the tissue has been secured.

It is the case with most prior art stapling instruments designed to sequentially place one or more lines of staples on both sides of an incision, that once the staple firing process begins, the surgeon must typically complete the entire stapling stroke. Otherwise, if the surgeon stops stapling mid-stroke, some of the staples will be only partially formed due to the terminated movement of the advancing camming member relative to the leading staple pushers. This can complicate the surgical procedure.

While prior art stapling and cutting instruments have proven useful, it would be beneficial to provide a surgeon with an instrument that provides greater control over staple placement along an incision during an endoscopic surgical procedure so as to alleviate the problems associated with a sequentially fired stapling instrument.

SUMMARY OF THE INVENTION

In one embodiment, the subject disclosure is directed to an instrument for stapling and cutting body tissue including a clamping jaw with an anvil wherein the anvil defines a slot and a pair of staple forming cups adjacent the slot, and a housing rotatably mounted on the anvil. A pusher rotatably mounts within the housing and a handle has a trigger for actuating the clamping jaw. A staple cartridge is within the housing and has a plurality of staples that sequentially slide into an aligned position with the pair of forming cups. A driver slidably mounts in the staple cartridge and couples to the pusher such that the driver forces a staple into the forming cups to staple the body tissue as the pusher rotates toward the anvil. A knife rotatably mounts on the staple cartridge and couples to the pusher such that the knife passes into the slot to cut the body tissue as the pusher rotates toward the anvil.

In another embodiment, the subject disclosure is directed to an instrument for stapling and cutting body tissue. The instrument includes a clamping jaw with an anvil defining an elongated slot and staple forming cups on opposing sides of the elongated slot. A housing rotatably mounts on the anvil and a pusher rotatably mounts within the housing. A handle actuates the clamping jaw by independently rotating the housing and the pusher towards the anvil. A staple cartridge, disposed in the housing, includes a staple track for retaining two rows of staples, each row being laterally spaced from the elongated slot. The drivers slidably mount in the staple cartridge and couple to the pusher such that each driver forces the distal most staple of each row into the forming cups and, in turn, staples the body tissue as the pusher rotates from the intermediate to closed position. A knife rotatably mounts on the staple cartridge and couples to the pusher such that the knife passes into the elongated slot and, in turn, cuts the body tissue as the pusher rotates from the intermediate to closed position.

In another embodiment, the subject disclosure is directed to a surgical instrument for stapling and cutting body tissue that includes a handle assembly with an actuation handle mounted for movement relative to a stationary handle. An elongated tubular body portion extends distally from the handle portion and defines a longitudinal axis. A fastening assembly is operatively connected to a distal end portion of the body portion and includes an elongated anvil portion having laterally opposed staple forming surfaces at a distal end thereof. The fastening assembly also includes an elongated housing portion mounted for pivotal movement relative to the anvil portion between an open position and a closed position. A cartridge is supported within the housing portion and it carries two laterally spaced apart longitudinally extending rows of staples. Each row of staples has a staple pusher movably mounted at a distal end thereof for urging staples from the cartridge. The cartridge also carries a cutting knife positioned between the laterally spaced apart rows of staples and mounted for pivotal movement about an axis extending at an angle with respect to the staple rows. A forked lever is also supported within the housing portion and it is mounted for pivotal movement relative to the cartridge. The forked lever has means for operatively engaging the staple pushers and means for operatively engaging the cutting knife. First and second actuation cables extend through the body portion between the handle assembly and the fastening assembly. The first actuation cable is operatively connected to the housing portion of the fastening assembly and second actuation cable is operatively connected to the forked lever of the fastening assembly.

In use, pivotal movement of the actuation handle relative to the stationary handle through a first distance causes the first actuation cable to move the housing portion from the open position, spaced from the anvil portion, to the closed position approximated with the anvil portion. Pivotal movement of the actuation handle through a second distance causes the second actuation cable to drive the lever into the cartridge, whereby the staple pushers drive respective staples from the cartridge to be formed against the staple forming surfaces of the anvil portion, while the cutting blade pivots about its axis in a path running between the staples driven from the cartridge.

Once the surgical stapler is inserted, it would be advantageous to provide a surgical stapling and cutting instrument whereby the distal end of the stapler articulates relative to an axis of the stapler for extending the distal end around bones, body tissue, and the like to orient and apply surgical staples from the distal end into body tissue. A need, therefore, exists in many such procedures for a compact surgical stapling and cutting instrument having an articulating distal end employing few moving parts for accurately positioning the distal end. In addition, the articulation mechanism should provide a stable articulated position at the distal end, allowing the distal end to be set in a fixed orientation by the operator as the operator directs the his/her hands to other activities.

It should be appreciated that the present invention can be implemented and utilized in numerous ways, including without limitation as a process, an apparatus, a system, a device, and a method for applications now known and later developed. These and other unique features of the system disclosed herein will become more readily apparent from the following description and the accompanying drawings.

BRIEF DESCRIPTION OF THE DRAWINGS

So that those having ordinary skill in the art to which the surgical apparatus and method of the subject invention appertains will more readily understand how to make and use the same, reference may be had to the drawings wherein:

FIG. 4 is a perspective view of the distal portion of the surgical instrument of FIG. 1 in an articulated position relative to the axis of the instrument body, with the staple cartridge assembly partially extended from the cartridge housing;

FIG. 5 is a detailed view taken along lines 5-5 of FIG. 2, illustrating the ratcheting interaction between the star wheel and pawl used to effectuate articulated movement of the stapling and cutting assembly relative to the axis of the instrument body;

FIG. 6 is a top elevational view of the distal portion of the instrument of FIG. 1 showing a portion of the range of motion of the stapling and cutting assembly of the instrument;

FIG. 9 is a detailed top view of a prong of the forked stapler pusher lever shown in FIG. 8;

FIG. 10 is a detailed side view of a prong of the forked stapler pusher lever shown FIG. 8;

FIG. 11 is a detailed top view of the staple forming cups of the anvil shown in FIG. 8;

FIG. 16 is a side elevational view of the surgical instrument of FIG. 1, partially cut-away to reveal the internal components of the handle assembly, wherein the movable trigger of the handle assembly is in a neutral position corresponding to the clamping jaw of the stapling and cutting assembly being positioned in a normally biased open position to receive tissue;

FIG. 17 an enlarged side elevational view, in cross-section, of the distal stapling and cutting assembly of the surgical instrument, with the clamping jaw in an open position;

FIG. 18 is a side elevational view of the surgical instrument of FIG. 1, partially cut-away to reveal the internal components of the handle assembly, wherein the movable trigger of the handle assembly is in an intermediate, partially closed, position relative to the fixed gripping handle, corresponding to the clamping jaw of the stapling and cutting assembly being moved to a closed position without firing the stapling mechanism;

FIG. 19 an enlarged side elevational view, in cross-section, of the distal stapling and cutting assembly of the surgical instrument, with the clamping jaw in a;

FIG. 20 is a side elevational view of the surgical instrument of FIG. 1, partially cut-away to reveal the internal components of the handle assembly, wherein the movable trigger of the handle assembly is in a fully compressed position relative to the fixed gripping handle, corresponding to the stapling and cutting mechanism in the clamping jaw being actuated to drive a pair of staples through body tissue captured in the clamping jaw while substantially simultaneously cutting the tissue between the staples with a pivoting knife blade;

FIG. 21 an enlarged side elevational view, in cross-section, of the distal stapling and cutting assembly of the surgical instrument, with the staple pusher pulled toward the anvil such that the staples are driven through the body tissue captured in the clamping jaw and formed in the cups of the anvil forming surface while the pivoting knife rotates about its axis to form an incision in the tissue between the staples;

FIG. 22 is a side elevational view of the surgical instrument, partially cut-away to reveal the internal components of the handle assembly, wherein the trigger is shown moving from the fully retracted position to the open position after firing the stapling mechanism, allowing the claming jaw to return to a normally biased open position;

FIG. 23 is a top view of a surgical site wherein tissue has been stapled and cut by the surgical instrument of FIG. 1, with the anvil beneath the tissue shown in detail;

FIG. 24 is a sectional view taken along lines 24-24 of FIG. 23, which shows a staple driven through tissue with the legs formed by the forming cups of the anvil surface.

DETAILED DESCRIPTION OF PREFERRED EMBODIMENTS

Figure 1:
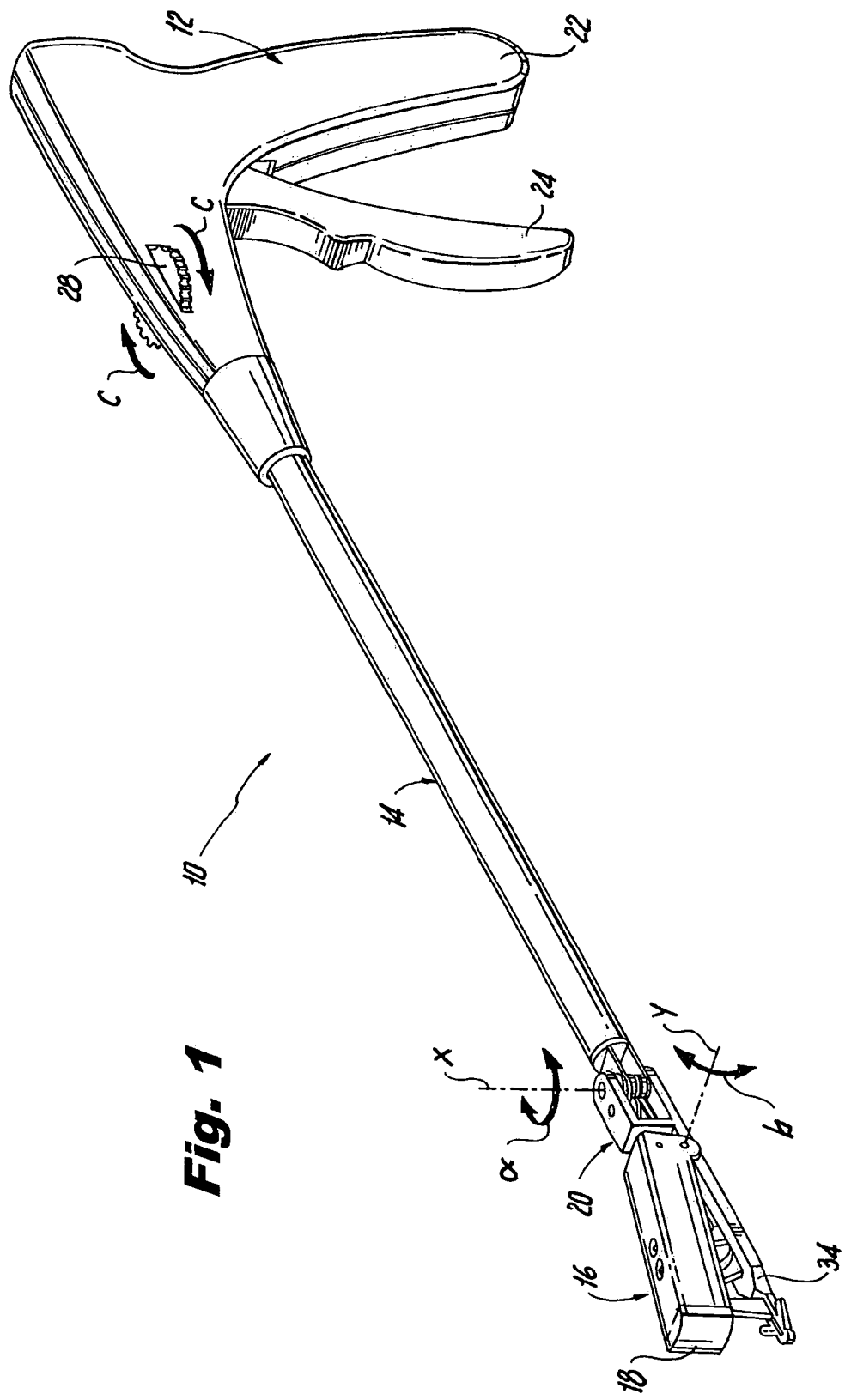
FIG. 1 is a perspective view of a surgical cutting and stapling instrument constructed in accordance with the present disclosure, with the distal clamping jaw oriented in an open position.

The present invention overcomes many of the prior art problems associated with endoscopic and laparoscopic stapling instruments. The advantages, and other features of the instrument disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

It is generally accepted that endoscopic procedures are more common than laparoscopic procedures. Accordingly, the following embodiments shall be discussed in terms of endoscopic procedures. However, use herein of such terms such should not be construed to limit the claims appended hereto to a cutting and stapling instrument for use only in conjunction with an endoscopic or laparoscopic tube. On the contrary, it is believed that the embodiments described herein may find use in any procedure where access is limited to a small incision. Also, as used herein the terms "fasteners" and "staples" shall be treated equivalently. Unless otherwise stated, the term "cartridge assembly" shall include at least the cartridge itself and staples or fasteners and staple drive members disposed therein. In the drawings and the description which follows, as is customary, the term "proximal" refers to the end which is closest to the operator when the instrument is in use, while the term "distal" will refer to the end which is furthest from the operator during use thereof. All relative descriptions herein such as left, right, up, and down are with reference to the Figures, and not meant in a limiting sense.

Following is a detailed description of the present instrument. The description is divided into separate sections to describe the structure and the desired movements produced thereby. Those sections include the instrument, the handle section, the steering assembly, the staple cartridge, the fastening and cutting assembly, the cable assembly, loading the instrument and firing the instrument. The following description is in reference to the drawings, wherein like reference numerals designate identical or corresponding parts throughout the several views.

The Instrument

Referring initially to FIG. 1 there is illustrated in perspective view the instrument 10 particularly adapted for cutting and applying surgical staples to body tissue. Except where noted otherwise, the materials utilized in the components of the apparatus generally include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) may also be utilized. However, equivalent alternative materials now known and later developed will readily come to the mind of those skilled in the art.

The instrument 10, as noted above, is configured to engage body tissue, progressively apply a plurality of surgical fasteners or staples thereto, while progressively forming an incision in the fastened body tissue during an endoscopic surgical procedure. In brief overview, the instrument 10 includes a handle portion 12, an elongated body portion 14 extending distally from the handle portion 12 defining a longitudinal axis, and a fastening and cutting assembly 16 supported on the distal end of the elongated body portion 14. The fastening and cutting assembly 16 is also referred to as a clamping jaw 16, particularly when loaded with a staple cartridge 18. A steering knuckle assembly or joint 20, between the fastening and cutting assembly 16 and handle portion 12, is adapted and configured to facilitate articulating motion of the assembly 16 about an axis "x" extending perpendicular to the longitudinal axis of body portion 14 through an arc denoted by arrow "a". The elongated body portion 14 is generally tubular to allow various cables to extend therethrough.

Referring still to FIG. 1, the handle portion 12 of the instrument 10 includes a stationary manual grip 22 and a pivotable trigger 24 which is mounted to be pivoted toward and away from the manual grip 22. To activate a firing linkage assembly 26 (see FIGS. 2, 3 and 8) and thereby start the cutting and stapling sequence, the trigger 24 is pivoted toward the manual grip 22 as described in further detail below. After firing, the trigger 24 pivots away from manual grip 22 to return the instrument 10 to the pre-fired position or open position for further stapling and cutting.

A manually operative ratcheting star wheel 28 is rotatable, about an axis denoted by arrow "c", to control the position of steering knuckle assembly 20. The star wheel 28 is conveniently positioned within the handle portion 12 to permit access by a user's fingers. In another embodiment, the handle portion 12 forms a relief for minimizing accidental rotation of the star wheel 28. Upon using the handle portion 12 and star wheel 28 to position the fastening and cutting assembly 16 in the desired location relative to the body portion 14, the trigger 24 is actuated to fire the instrument 10, as discussed in greater detail below.

Referring to FIG. 4, the fastening/stapling and cutting assembly 16 houses a removable staple cartridge 18 within a housing 32. In a normally biased open position, the staple cartridge 18 can be manually inserted or removed as desired in a direction extending along arrow "d" as shown in FIG. 4. The housing 32 is pivotally attached and normally biased open to permit the insertion or capture of body tissue therein as shown in FIG. 16. The combined staple cartridge 18 and housing 32 pivot about axis "y" denoted through an arc denoted by arrow "b"through the manual movement of the trigger 24. As a result, the staple cartridge 18 drives against an anvil 34 to form the staples and incision is formed by a knife associated with the cartridge. Structure to accomplish driving the staple cartridge 18 against the stapler anvil 34 and forming an incision in the stapled tissue is provided. Such structure includes, among other things, cables that are operatively connected to the trigger 24 such that, when the trigger 24 is actuated, preferably repeatedly, the surgical instrument 10 is fired multiple times to progressively cut and apply staples to body tissue. It is envisioned that many other types of linkages than cables would perform adequately within the subject instrument as would be appreciated by those of ordinary skill in the pertinent art.

The Handle Section

Figure 2:
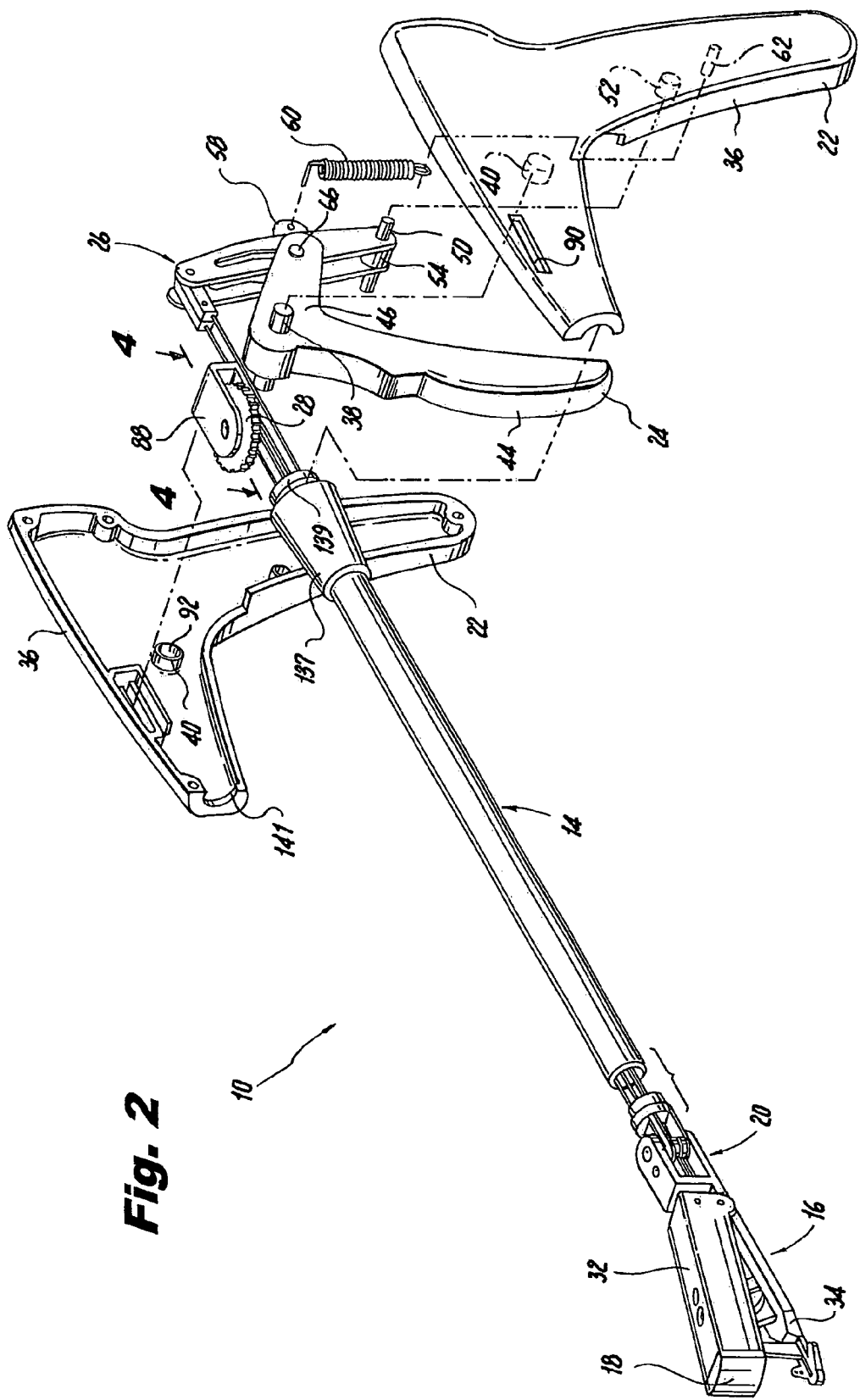
FIG. 2 is an exploded perspective view, with parts separated for ease of illustration, of the handle assembly of the instrument of FIG. 1.
Figure 3:
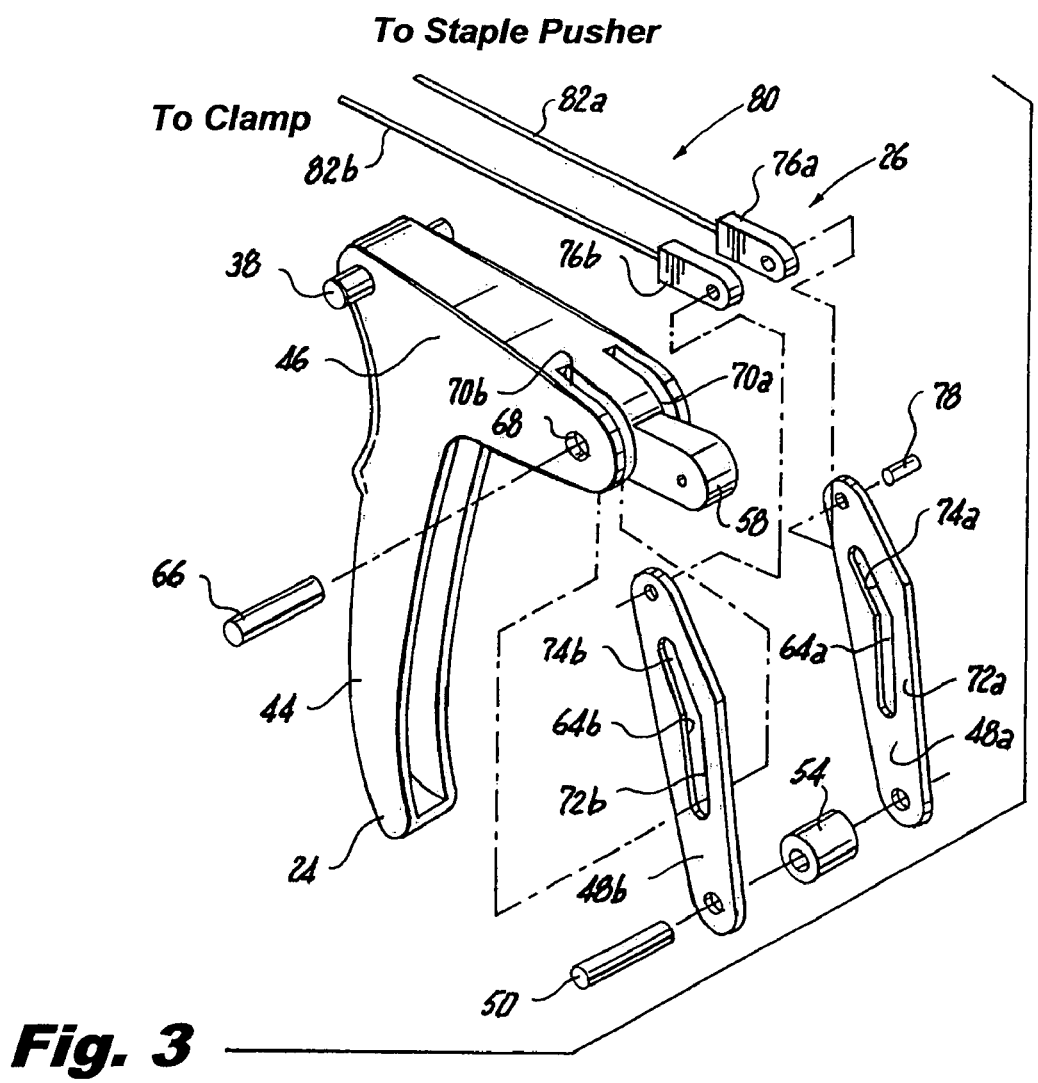
FIG. 3 is an exploded perspective view, with parts separated for ease of illustration, of the trigger linkage subassembly of the handle assembly of the surgical instrument of FIG. 1.

Referring now to FIGS. 2 and 3, there are shown two perspective views of the handle portion 12 with parts separated for illustration purposes. The handle portion 12 allows a user to position the instrument 10 and control both the steering assembly and instrument firing as described below.

The handle portion 12 is comprised of a two-piece handle 36 preferably as shown and preferably formed of polycarbonate material. The separate parts of the housing 32 may be attached by welding, adhesives, screws (as shown) and the like. The ultimate purpose of the handle portion 12 is to provide controlled movement of the fastening and cutting assembly 16. The trigger 24 is pivotally mounted to the handle 36 by pivot pin 38. Opposing bosses 40 on the inside of the handle 36 form recesses 42 for receiving the pivot pin 38. The trigger 24 is roughly L-shaped with a trigger arm 44 being squeezed by the surgeon and a lever arm 46 for translating force from the trigger arm 44 to drive the firing linkage assembly 26.

The firing linkage assembly 26 has two cam portions 48a, 48b driven by the lever arm 46. Each cam portion 48a, 48b independently pivots at a lower end about a pin 50 received in shoulders 52 formed in the handle 36. A bushing 54 laterally separates the cam portions 48a, 48b and allows independent rotation thereof. A rearward projection 58 on the trigger 24 passes intermediate the cam portions 48a, 48b and connects to a spring 60, which extends to a retaining post 62 of the handle 36. The trigger 24 is biased by the spring 60 to an open position.

Each cam portion 48a, 48b forms cam tracks 64a, 64b, respectively, for slidably receiving a cam pin 66 captured in a transverse bore 68 of the lever arm 46. The cam portions 48a, 48b slide into respective slots 70a, 70b formed in the lever arm 46. In the open position, the cam pin 66 is preferably at the bottom of the cam tracks 64a, 64b. Each cam track 64a, 64b is uniquely shaped to achieve the desired results described in more detail below. In a preferred embodiment, the cam tracks 64a, 64b have a linear section 72a, 72b and an angled section 74a, 74b. The angled section 74a is relatively more slanted with respect to the linear section 74a so that the resulting motion thereof is relatively greater as the trigger 24 moves to the closed position.

Swing blocks 76a, 76b pivotally mount to the top of the cam portions 48a, 48b by pin 78. The swing blocks 76a, 76b also retain cables 82a, 82b, respectively, of the cable assembly 80. As described hereinbelow, actuation of the trigger 24 causes proximal movement of the cam portions 48a, 48b such that the cables 82a, 82b are tensioned to fire the instrument (e.g., close the clamping jaw 16, staple tissue and cut tissue). As can be seen, the firing linkage assembly 26 serves to translate force from the trigger 24 to the fastening and cutting assembly 16 and, as such, many means for this function would be apparent to those of ordinary skill in the art based upon review of the subject disclosure.

The Steering Assembly

Referring to FIG. 2, the steering knuckle assembly 20 includes the manually adjustable star wheel 28 mounted on the handle 36 and connected by a steering cable 86 to a steering knuckle assembly 20. The steering knuckle assembly 20 allows the user to vary and set the angular relationship between the fastening and cutting assembly 16 and the elongated body portion 14 such that further manipulation is not required. As a result, the user can pay undivided attention to locating and firing the instrument 10. FIG. 6 shows the steering knuckle assembly 20 out of alignment with the longitudinal axis of the elongated body portion 14 and in phantom lines to illustrate an acceptable range of movement about the axis "x".

Referring to FIGS. 2 and 5, the handle 36 secures a bracket 88 having the star wheel 28 rotatably mounted thereon. Apertures 90 on opposing sides of the handle 36 allow the star wheel 28 to protrude from the handle 36 and, thereby, be accessed by the user. In order to prevent free rotation of the star wheel 28, a spring clip 92 secures to the bracket 88 and forms a tip 94 for engaging teeth 96 formed in the star wheel 28. The spring clip 92 is sized and configured such that normal manual pressure overcomes the retentive force thereof. The star wheel 28 also forms a pulley portion 98, which couples to the steering cable 86. The steering cable 86 forms an elongated loop attached to the pulley portion 98 at one end and attached to the steering knuckle assembly 20 at the other end as described below.

Figure 7:
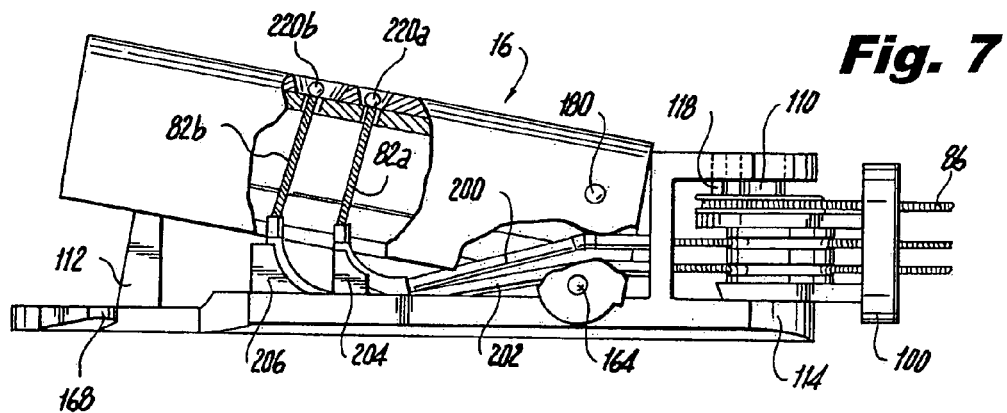
FIG. 7 is aside elevational view, in partial cross-section, of the distal stapling and cutting assembly, wherein the staple cartridge is removed from the cartridge housing.
Figure 8:
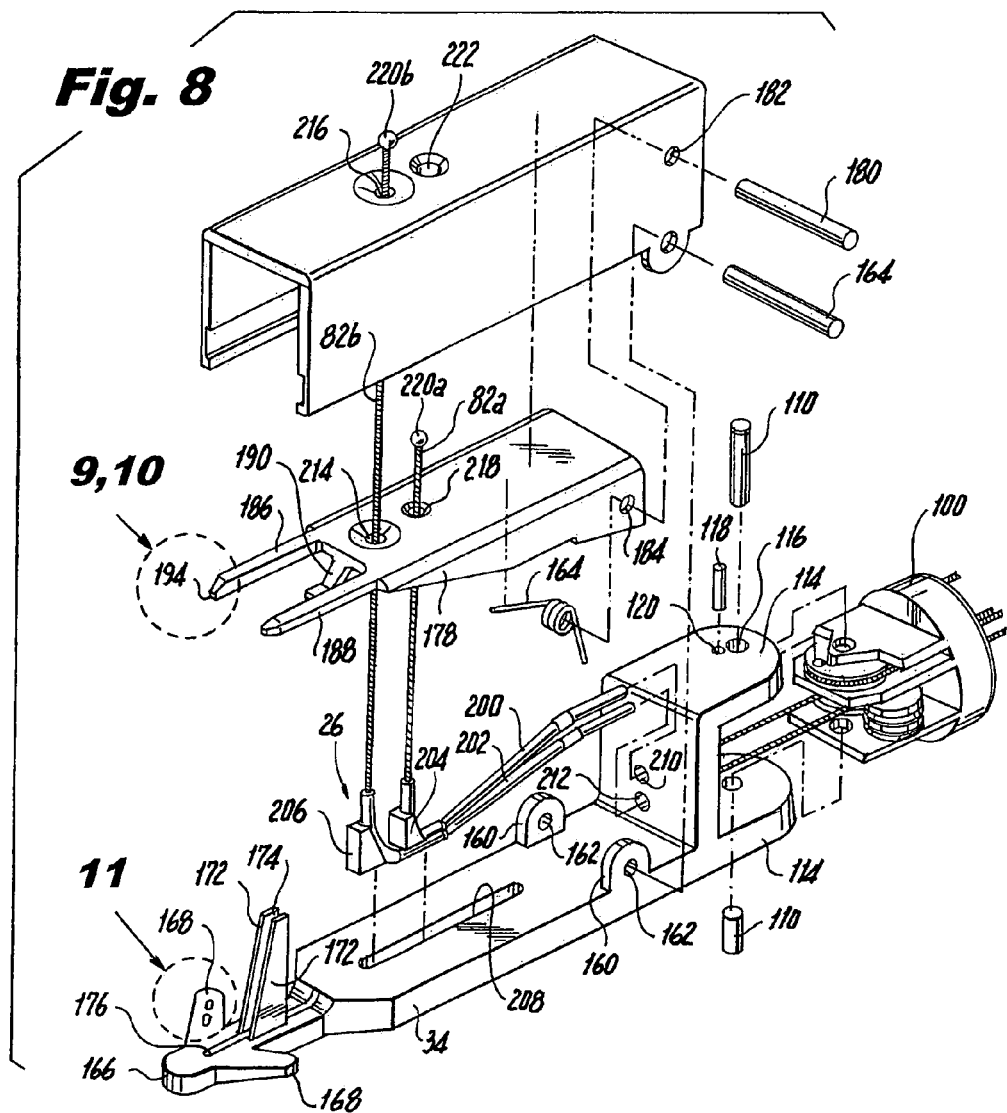
FIG. 8 is an exploded perspective view of the distal stapling and cutting assembly of FIG. 7, with parts separated for ease of illustration.
Figure 12:
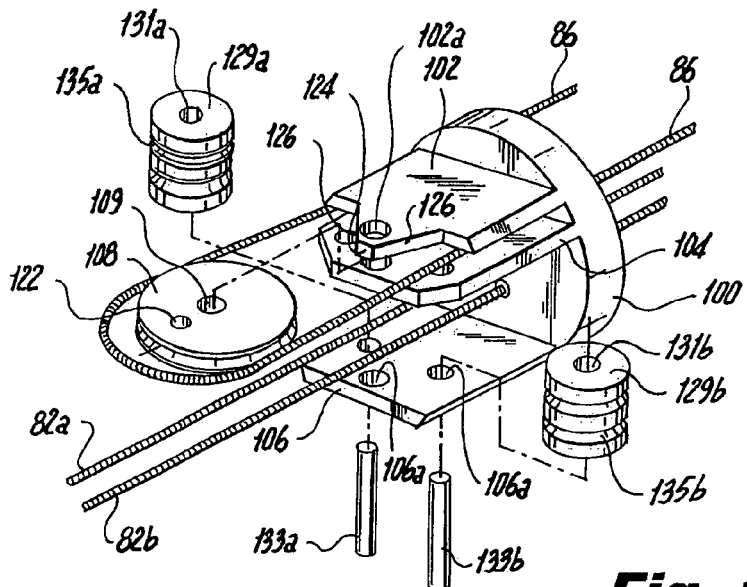
FIG. 12 is an exploded perspective view, with parts separated for ease of illustration, of the jointed steering knuckle assembly of the surgical instrument of FIG. 1.

Referring now to FIGS. 7, 8 and 12, the steering cable 86 passes through the elongated body portion 14 to a termination block 100. A proximal side of the termination block 100 is adapted and configured to plug the elongated portion 14 by a friction fit. The termination block 100 also forms apertures for allowing the steering cable 86 and other cables to pass without obstruction. A distal side of the termination block 100 includes three legs 102, 104, 106 with transverse bores 102a, 104a, 106a, respectively. A pulley 108 is rotatably secured between the top leg 102 and the middle leg 104 by a central aperture 109 that receives a pin 110. The pulley 108 receives the steering cable 86 such that rotation of the star wheel 28 causes a corresponding rotation of the pulley 108.

The stapler anvil 34 of the fastening and cutting assembly 16 rotatably couples to the termination block 100 and is keyed to the pulley 108. The stapler anvil 34 has a clevis formed by opposing upper and lower legs 114, each with a transverse bore 116 for receiving the pivot pin 110. Thus, the stapler anvil 34 is rotationally coupled to the termination block 100. To key and, thereby, drive the rotational motion of the stapler anvil 34, a pin 118 extends into bores 120, 122 formed in the upper leg 102 and pulley 108, respectively. Thus, as the pulley 108 moves so does the stapler anvil 34. The range of motion of the stapler anvil 34 is limited by the shape of the top leg 102 of the termination block 100, which comes to a point 124. Adjacent the point 124 are angled surfaces 126 that act as hard stops for the pin 118 to limit the rotation of the stapler anvil 34. Thus, rotation of the star wheel 28 turns the pulley 108 and, ultimately, the stapler anvil 34, e.g., the fastening and cutting assembly 16, rotates about the axis "x" as shown in FIG. 6. A pair of capstans 129a, 129b rotatably mount to the termination block 100 for varying routing of the cables 82a, 82b, respectively. Each capstan 129a, 129b is fixed to the termination block 100 by respective pins 133a, 133b in a central aperture 131a, 131b formed therein. The capstans 129a, 129b also form circumferential grooves 135a, 135b, respectively, for routing the cables 82a, 82b around the capstans 129a, 129b.

Referring in particular to FIG. 2, in one embodiment, the proximal portion of the tubular body portion 14 is rotatably mounted to the handle portion 12 to facilitate axial rotation of the body portion 14 relative to the handle portion 12. The tubular section forms a hub 137 for rotational adjustment. An annular rim 139 protrudes from the hub 137 to form a groove that is tightly captured by an opening 141 in the handle portion 12.

The Staple Cartridge

Figure 13:
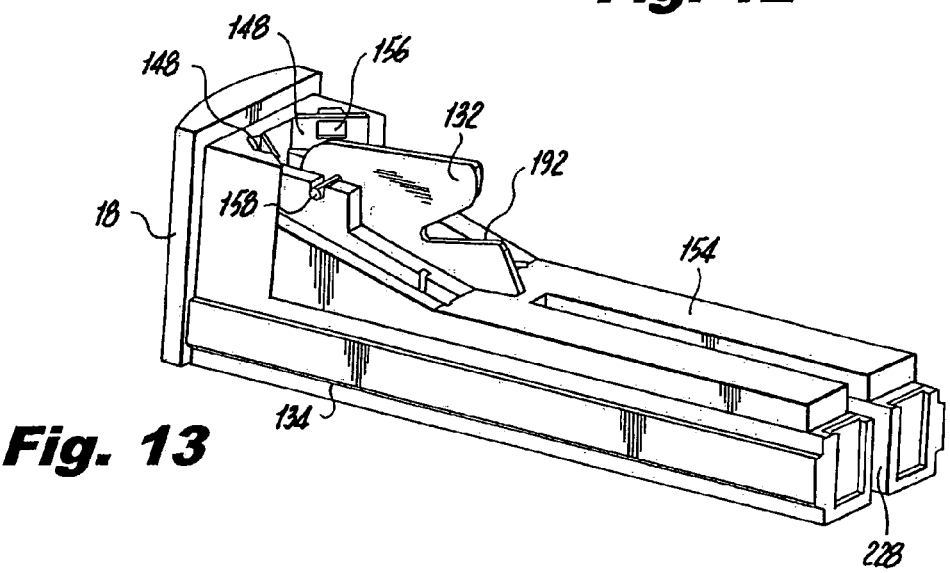
FIG. 13 is a perspective view of the staple cartridge assembly of the instrument of FIG. 1, as viewed from a proximal end thereof.
Figure 14:
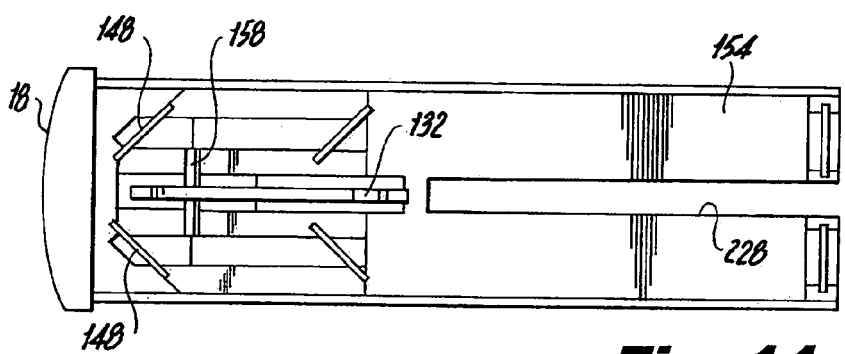
FIG. 14 is a top plan view of the staple cartridge assembly of shown in FIG. 13.
Figure 15:
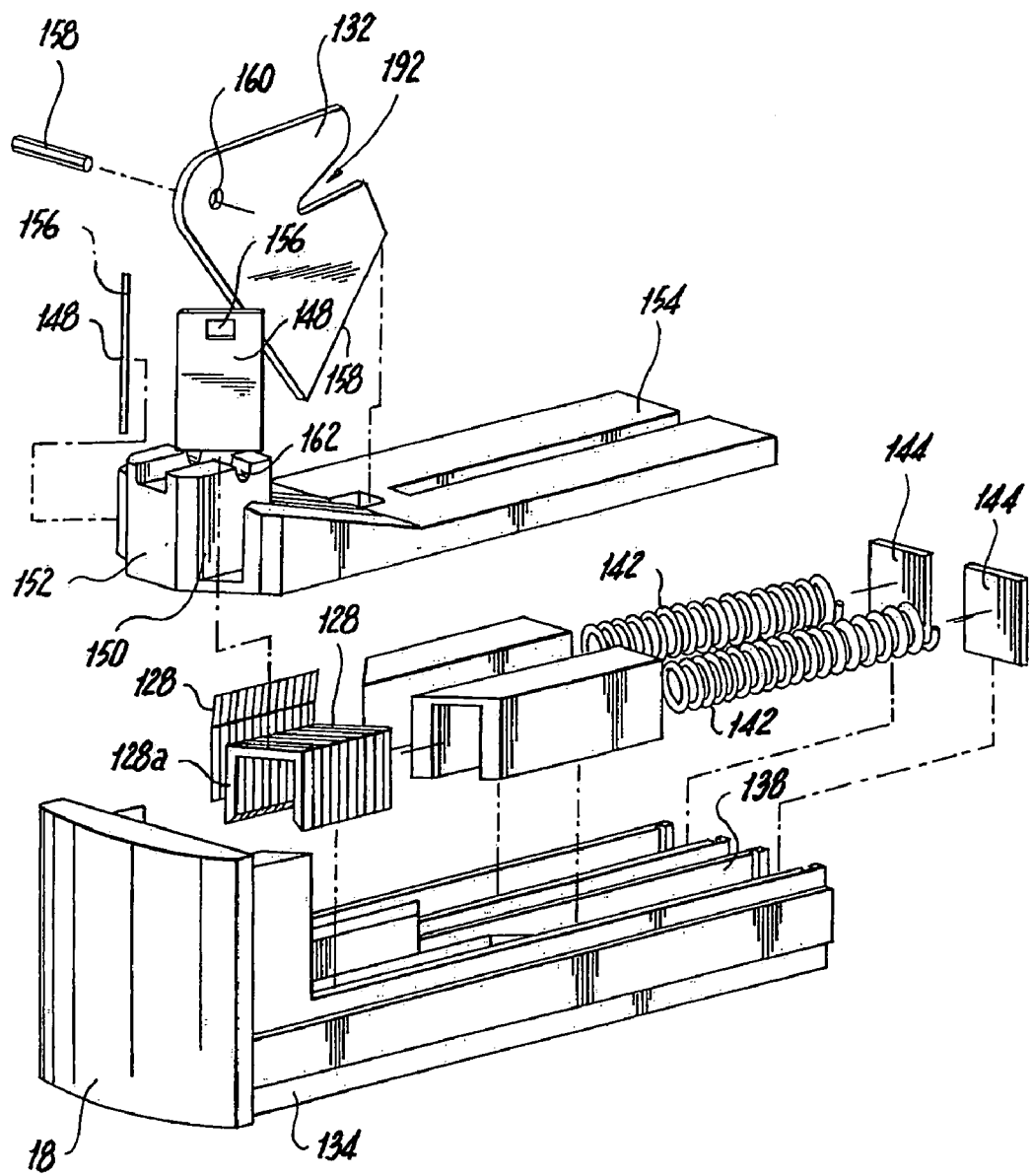
FIG. 15 is a perspective view of the staple cartridge assembly of FIG. 13, with parts separated for ease of illustration.

Referring now to FIGS. 13-15, there are shown a perspective view, a top view and a view with parts separated for illustration purposes, respectively, of the staple cartridge 18 of the instrument 10. The staple cartridge 18 retains a plurality of staples 128, in two rows, for deployment in tissue as well as a knife 132 for cutting tissue. As described hereinabove, the staple cartridge 18, when assembled, is inserted or loaded into the fastening and cutting assembly 16. It is envisioned that one or more staple cartridges 18 may be provided with the instrument 10. The staple cartridge 18 may be disposable or sterilized and re-loaded with additional staples 128 for re-use.

The staple cartridge 18 is comprised of a staple track 134 for supporting the two rows of staples 128. The staples 128 are roughly U-shaped such that depending legs 128a rest in parallel elongated channels 138. The staples 128 are set at an angle with respect to the length of the rows in order to form at an angle with respect to the incision. Of course, the staples 128 could also be set perpendicularly or even parallel with respect to the length of the rows. In one embodiment, the rows of staples 128 are joined by an adhesive and, in another embodiment, each staple 128 is individually loaded into the elongated channels 138. The staples 128 are biased to the distal most position in the channels 138 by elongated staple guides 140, which compress a respective staple feed spring 142. The staple guides 140 are also rough U-shaped in cross-section and angled at the distal most end to substantially engage the staples 128. The staple feed springs 142 are retained in the channels 138 by spring retainers 144 disposed in the proximal most end of the channels 138. The spring retainers 144 are plate-shaped and frictionally fit within transverse grooves 146 formed in the staple track 134.

Referring in particular to FIG. 15, a frame 154 nestles on top of the staple track 134 for carrying staple forming blades 148 and the pivoting knife 132. The staple forming blades 148 are slidingly held in opposing channels 150 formed in a mounting block 152 at the distal end of the frame 154 such that each blade 148 aligns above the distal most staple 128 of each row. Preferably, a thickness of the blades 148 is equal to or slightly less than that of the staples 128. Apertures 156 formed in the blades 148 receive means that drive downward to form the staples as is described hereinbelow.

The mounting block 152 also locates and positions a cutting edge 158 of the knife 132 for pivotal motion during firing. The knife 132 is pivotally retained by a pin 158 passing through an aperture 160. On each side of the aperture 160, the pin 158 is secured to a semi-circular cradle 162 formed in the mounting block 152. The pin 158 may be spot welded or other well known means for attachment as would be appreciated by those of ordinary skill in the pertinent art.

The Fastening and Cutting Assembly

Referring now to FIG. 8, there is shown a perspective view, with parts separated for illustration purposes, of the fastening and cutting assembly 16 of the instrument 10. The fastening and cutting assembly 16 retains the staple cartridge 18 and drives the staple forming blades 148 and knife 132 to accomplish the stapling and cutting of body tissue. The fastening and cutting assembly 16 is normally biased open by a spring 164 mounted between the housing 32 and the stapler anvil 34. As noted above with respect to FIG. 6, the stapler anvil 34 of the fastening and cutting assembly 16 interacts with the steering knuckle assembly 20 such that the fastening and cutting assembly 16 is easily positioned at a desired angle with respect to the elongated body portion 14.

The stapler anvil 34 also includes a narrowed distal end 166 with a pair of wing-shaped lateral projections 168. The wing-shaped lateral projections 168 vertically align with the distal most staple 128 and staple blades 148. Referring in particular to FIG. 11, forming cups 170 in each lateral projection 168 capture and shape the staple legs 128a during firing. Two upstanding members 172 on the distal end 166 also form a knife passageway 174 for guiding the knife 132. During cutting, the knife cutting edge 158 passes through an elongated slot 176 formed at a bottom of the knife passageway. The upstanding members 172 also serve as a tissue stop to control the amount of tissue that is cut on each stroke of the instrument, and to ensure that an equal amount of tissue is cut each time. The stapler anvil 34 has two upstanding ears 160 that form apertures 162 such that the housing 32 is rotatably coupled thereto by a pin 164. As a result, the housing 32 can pivot upward for loading the staple cartridge 18 and downward during firing of the instrument 10.

The fastening and cutting assembly 16 is also includes a staple pusher 178, which functions as a lever and is rotatably coupled to the housing 32 at a proximal end by another pin 180 passing through holes 182, 184 formed in the housing 32 and staple pusher 178, respectively. The distal end of the staple pusher 178 has two prongs 186, 188 for driving the staple forming blades 148 and a third prong 190 for driving the knife 132 during firing. The third prong 190 is relatively shorter and depends below the other two prongs 186, 188 to align and couple with a notch 192 of the knife 132.

Referring in particular to FIGS. 9 and 10, enlarged detail top and side views, respectively, of the distal most tip 194 of prong 186 are shown. The tips 194 are shaped and configured to repeatedly and assuredly engage the apertures 156 of the staple forming blades 148. Preferably, the tip 194 is chamfered such that a surface 196 of the tip 194 aligns vertically with the staple forming blades 148 and, thereby, the aperture 156 therein. The tip of prong 188 is also similarly asymmetrically chamfered although not shown in enlarged detail for simplicity.

The Cable Assembly

Referring to FIGS. 1, 2, 7, and 8, the cable assembly 80 extends from the handle portion 12 for transmitting the force applied to the trigger 24 to the fastening and cutting assembly 16 during firing of the instrument 10. The cable assembly 80 includes the clamping cable 82b for initially closing the housing 32 and the staple form and cut cable 82a for subsequently pulling the staple pusher 178 downward.

Referring in particular to FIG. 8, the cable assembly 80 terminates in the fastening and cutting assembly 16. The cable assembly 80 has a first cable guide tube 200 and a second cable guide tube 202, each of which consists of a plurality of segments articulated into a roughly arcuate shape. Each guide tube 200, 202 has a mounting block 204, 206 at a proximal end, respectively, for frictionally engaging an elongated slot 208 in the stapler anvil 34. At a distal end, the guide tubes 200, 202 pass into holes 210, 212, respectively, formed in the stapler anvil 34. As a result, the guide tubes 200, 202 form a passageway for routing the cables 82a, 82b, respectively, upwards toward the housing 32.

At the proximal end, the clamping cable 82b passes upward through a hole 214 in the stapler pusher 178 and a hole 216 in the housing 32. A ball, knot or other well known means 220b formed at the end of the clamping cable 82b retains the end of the clamping cable 82b above the housing 32. As the clamping cable 82b is pulled downward, the force is transmitted to the housing 32 and, in turn, the housing 32 rotates along arrow "b" as shown in FIG. 1. Similarly, the staple form and cut cable 82a passes upward through a hole 218 in the staple pusher 178 and is retained above the staple pusher 178 by a ball 220a. A hollow 222 formed in the housing 32 prevents interference between the ball 220a so that the staple pusher 178 flushly nestles therein. As a result, the staple pusher 178 rotationally moves with the housing 32 but can also be drawn downward independently by staple form and cut cable 82a. In another embodiment, a single cable extends from the trigger 24 so that the housing 32 is pulled toward the anvil 34 in a single action to cut and staple the body tissue.

Loading the Instrument

Referring to FIGS. 13-15, the staple cartridge 18 is loaded with staples 128 prior to insertion within the housing 32. To load the staple cartridge 18, the right and left staple guides 140 are retracted proximally, independently or together, and staples 128 are inserted in the elongated channels 138. Upon release of the staple guides 140, the staples 128 are pushed to a proximal most position within the elongated channels 138.

Referring now to FIG. 4, once the staple cartridge 18 has a desired number of staples 128, the cartridge 18 is ready for insertion in the instrument 10. The housing 32 defines a channel 224 in each opposing sidewall for slidably engaging strips 226 to set a position of the staple cartridge 18 within the housing 32. A passage slot 228, best seen in FIGS. 13-15, formed by the pusher frame 154 and staple track 134 provides clearance so that the insertion of the staple cartridge 18 does not interfere with the cable assembly 80. The staple cartridge 18 is moved proximally within the channels 224 until the staple cartridge 18 is flush with the distal most end of the housing 32.

It is envisioned that the staple cartridge 18 and/or the instrument 10 may be preloaded by a machine as would be known to those of ordinary skill in the art or manually loaded in a sterile environment. In one embodiment, the instrument 10 comes loaded with a single staple cartridge 18 and is entirely disposable. It is also contemplated that the tubular section 14 is selectively detachable at the steering knuckle assembly so that the handle portion 12 and tubular section 14 may be sterilized and reused. Alternatively just the staple cartridge 18 is disposable.

Firing the Instrument

1. The Open Position

As the mechanical structure and connections have now been described to produce the movements of the instrument 10, the application of the instrument 10 to staple and cut a portion of body tissue will now be described sequentially. Referring to FIGS. 16 and 17, an instrument 10 with a fully loaded staple cartridge 18 is shown with the clamping jaw 16 loaded with a cartridge 18 in an open position. The clamping jaw 16 is open without pressure on the trigger 24 because the bias spring 52 pulls the cam portions 48a, 48b downward until the cam pin 66 bottoms out in the cam tracks 64a, 64b. Thus, the trigger 24 is extended distally and a minimal tautness is applied to the cable assembly 80.

2. Locating the Instrument

The handle portion 12 is held and used to direct the clamping jaw 16 to a desired location. As best seen in FIGS. 5, 6 and 12, by spinning the star wheel 28, the steering knuckle assembly 20 is used to orient the clamping jaw 16 as desired. Once in a desired position, the clamping jaw 16 is placed about a portion of body tissue 232 to be stapled and cut. The body tissue 232 is tucked between the staple cartridge 18 and anvil 34, up against the upstanding member 172 of the stapler anvil 34.

3. The Intermediate Position

Figures 18, 19:
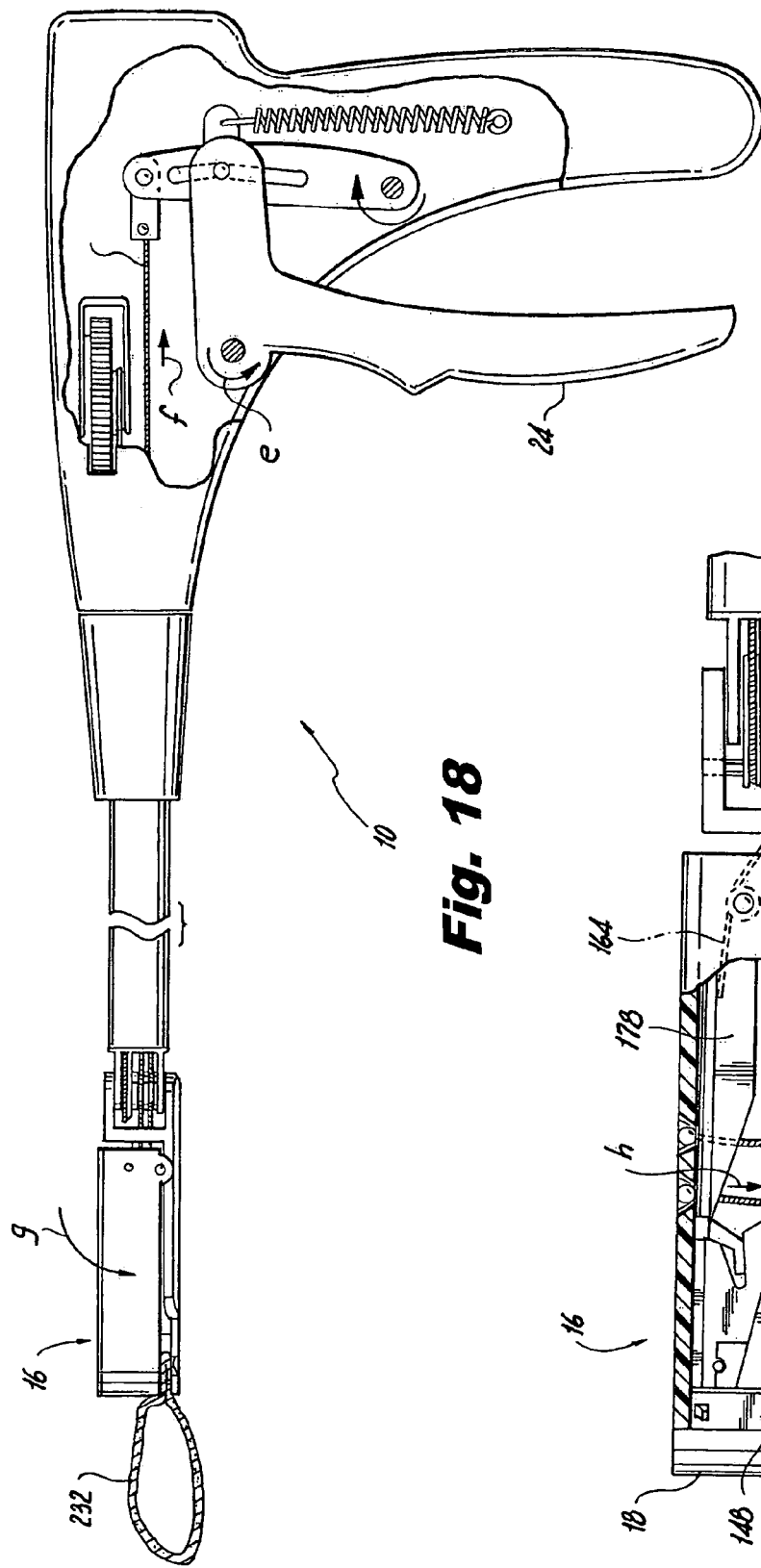

Referring to FIGS. 18 and 19, the trigger 24 is squeezed to an intermediate position. The trigger 24 and cam tracks 64a, 64b are sized and configured such that the rotational motion shown by arrow "e" causes a substantially linear motion of the swing blocks 76a, 76b as shown by arrow "f". However, the resulting effect on cables 82a, 82b is different because of the varying configurations of the cam tracks 64a, 64b. In this intermediate position, the clamping cable 82b becomes taut enough to move the housing 32 along arrow "g" to a closed position. In effect, the clamping jaw 16 closes such that the body tissue 232 becomes flattened between the staple cartridge 18/housing 32 and stapler anvil 34.

In more detail and as best seen in FIGS. 2, 3 and 19, as the trigger 24 pivots about pin 37 toward the intermediate position, the cam pin 66 moves upward in the cam tracks 64a, 64b to rest substantially intermediate the straight sections 72a, 72b and the angled sections 74a, 74b and, thereby, the top of the cam portions 48a, 48b are forced in a proximal direction. Thus, the swing block 76b, attached to the cam portion 48b, pulls the clamping cable 82b proximally. In another embodiment, detents or hollows (not shown) are formed at the transition form the straight sections 72a, 72b and the angled sections 74a, 74b in order to retain the trigger 24 in the intermediate position and provide the user with a manual indication of achieving the intermediate position. As best seen in FIGS. 8 and 19, when the clamping cable 82b is pulled in a proximal direction, the housing 32 is pulled downward by the end ball 234 and rotates about pin 164. The housing 32 overcomes the force of bias spring 164 and pivots downward on pin 164 along arrow "h" to close the clamping jaw 16. In another embodiment, the staple form and cut cable 82a becomes equally as taut as the clamping cable 82b in the intermediate position to facilitate closing the clamping jaw 16.

Once closed, the body tissue 232 is secured in position between the staple cartridge 18/housing 32 and stapler anvil 34 for stapling and cutting. Although the staple pusher 178 has moved with the housing 32, the staple pusher 178 remains adjacent the housing 32 and spaced from the body tissue 232. The body tissue 232 is flattened above the wing-shaped lateral projections 168 and proximal end of the elongated slot 176 of the stapler anvil 34. As best seen in FIG. 19, the prongs 186, 188 of the staple pusher 178 are disposed in the staple forming blades 148 and the third prong 190 is disposed in the notch 192 of the knife 132.

4. The Stapled and Cut Position

Referring to FIGS. 20 and 21, the trigger 24 is squeezed to a stapled and cut position adjacent the handle portion 12. The trigger 24 and cam track 64a are sized and configured such that the further rotational motion shown by arrow "h" causes a further linear motion of the swing block 76a as shown by arrow "i". As a result, the staple form and cut cable 82a becomes taut and moves the staple pusher 178 as denoted by arrow "j". In turn, the body tissue 232 is substantially simultaneously cut and stapled on opposing sides of the incision.

In more detail and as best seen in FIG. 2, as the trigger 24 pivots about pin 37 from the intermediate position, the cam pin 66 moves upward to the top position in the cam tracks 64a, 64b and, thereby, the top of the cam portion 48a is moved further in a proximal direction. Thus, the swing block 76a, attached to the cam portion 48a, pulls the staple form and cut cable 82a proximally.

As best seen in FIGS. 8 and 21, when the staple form and cut cable 82a is pulled in a proximal direction, the staple pusher 178 is pulled by the end ball 220 and rotates about pin 180 as denoted by arrow "j". By the disposition of the prongs 186, 188 in the staple forming blades 148, the staple pusher 178 forces the staple forming blades 148 downward against the staples 128 as denoted by arrow "k". Each staple forming blade 148 pushes a staple 128 downward through the body tissue 232 such that the legs 128a curl inward into the body tissue as shown in FIG. 24. At the same time, disposition of the prong 190 in the knife 132, forces the knife 132 to rotate along arrow "l" into the passageway 174 and elongated slot 176 to thereby, cut the body tissue 232 adjacent the elongated slot 176.

Figure 25:
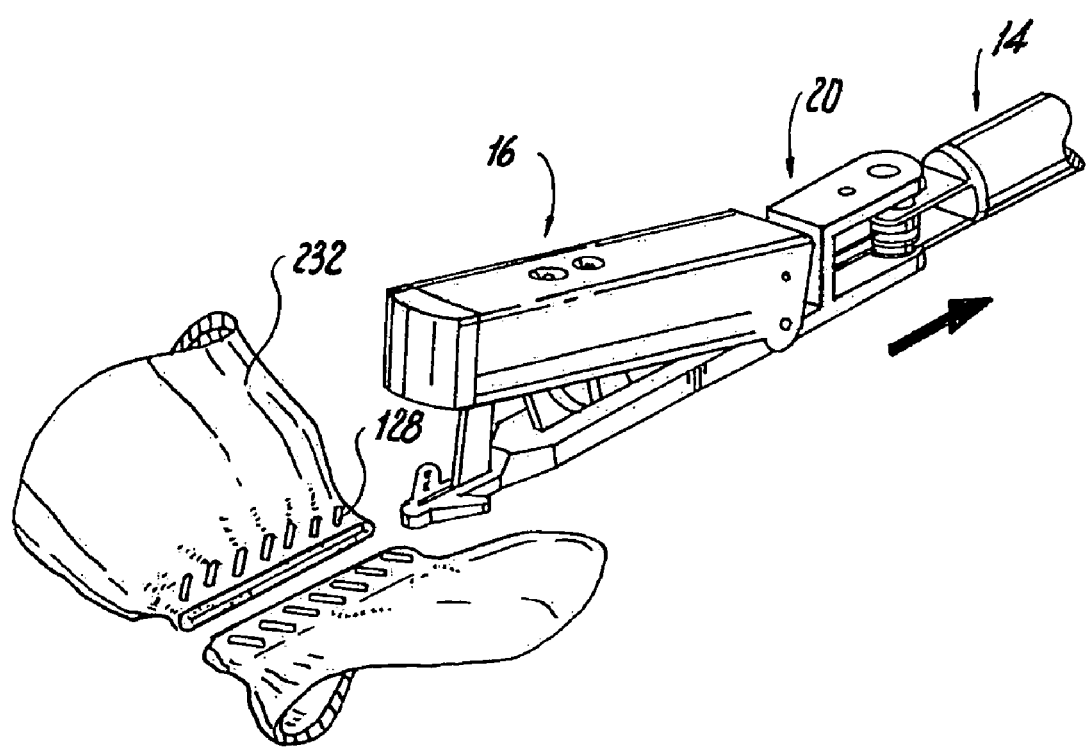
FIG. 25 is a perspective view of the stapling and cutting assembly of the surgical instrument of FIG. 1, as it is being withdrawn from a surgical site wherein two lines of staples have been progressively applied to body tissue that has been substantially simultaneously cut.

Referring now to FIGS. 23-25, once driven through the body tissue 232, the knife cutting edge 158 creates an elongated incision 236. On opposing sides of the incision 236, a pair of staples 128 fasten portions of the body tissue 232 together. These staples 128 are offset at an angle with respect to the incision 236 but the staples could be positioned anywhere between parallel and perpendicular the incision 236 as would be appreciated by those of ordinary skill in the pertinent art.

Referring now to FIG. 22, after cutting and stapling the body tissue 232, the instrument 10 returns to the open position by release of the trigger 24 to reverse the sequence of motions described above. Upon release, the spring 60 pulls the rearward projection 58 downward and, thereby, the trigger 24 pivots on pin 50 and moves away from the handle portion 12 as denoted by arrow "m". The cam pin 66 comes to rest in the bottom of the cam tracks 64a, 64b and this motion is translated into the swing blocks 76a, 76b and cables 82a, 82b moving distally as denoted by arrow "n". With the removal of tension upon the cables 82a, 82b and, in turn, the housing 32 and staple pusher 178, the bias spring 164 opens the clamping jaw 16 as denoted by arrow "o". Once again open, the instrument 10 is ready to continue stapling and cutting to lengthen the incision 236 while fixing the body tissue 232 on each side with additional staples 128.

While the subject invention has been described with respect to preferred embodiments, those skilled in the art will readily appreciate that various changes and/or modifications can be made to thereto without departing from the spirit or scope of the invention as defined by the appended claims.

What is claimed is:

1. An instrument for stapling and cutting body tissue comprising:
    a) a clamping jaw including an anvil, a housing rotatably mounted on the anvil, and a pusher rotatably mounted within the housing, wherein the anvil defines a slot and at least one pair of staple forming cups adjacent the slot;
    b) a handle having a trigger operatively connected to the clamping jaw for actuating the clamping jaw; and
    c) a staple cartridge within the housing, the staple cartridge including at least one staple aligned with the pair of forming cups, a driver slidably mounted in the staple cartridge, aligned with the at least one staple, and coupled to the pusher such that the driver forces the staple into the forming cups to staple the body tissue as the pusher rotates toward the anvil, and a knife rotatably mounted on the staple cartridge and coupled to the pusher such that the knife passes into the slot to cut the body tissue as the pusher rotates toward the anvil.

2. An instrument as recited in claim 1, further comprising an elongated body portion extending between the clamping jaw and handle.

3. An instrument as recited in claim 2, wherein the elongated body portion has means for articulating the clamping jaw.

4. An instrument as recited in claim 3, wherein the means for articulating includes a manual wheel rotatably mounted on the handle, a steering knuckle assembly intermediate the elongated body and clamping jaw, and a steering cable extending between the manual wheel and steering knuckle assembly for translating movement of the manual wheel into movement of the steering knuckle assembly.

5. An instrument as recited in claim 1, wherein the at least one staple is at an angle with respect to the slot and the knife.

6. An instrument as recited in claim 1, wherein the at least one pair of staple forming cups is two pairs of staple forming cups on opposing sides of the slot and the at least one staple is two rows of staples, wherein a single staple of each row aligns with the two pair of forming cups, respectively.

7. An instrument as recited in claim 1, further comprising a cable assembly, extending from the handle to the clamping jaw, for transmitting force applied to the trigger to fire the clamping jaw, the cable assembly including a clamping cable for rotating the housing toward the anvil and a staple/cut cable for rotating the pusher toward the anvil.

8. An instrument as recited in claim 7, wherein the cable assembly further includes guide tubes surrounding at least a portion of the clamping cable and the staple/cut cable.

9. An instrument as recited in claim 7, further comprising a firing linkage assembly between the trigger and cable assembly, the firing linkage assembly having:
    two cam portions driven by the trigger, wherein each cam portion independently pivots at a lower end about a pin coupled to the handle, each cam portion forming cam tracks for slidably receiving a cam pin captured in the trigger such that each cam track moves independently; and swing blocks pivotally mounted to each cam portion and coupling to the clamping cable and the staple/cut cable, respectively, such that actuation of the trigger causes movement of the cam portions and thereby tensioning of the clamping cable to rotate the housing to hold and flatten the body tissue, then tensioning of the staple/cut cable to rotate the pusher to cut and staple the body tissue.

10. An instrument for substantially simultaneously stapling and cutting body tissue comprising:
   a) a fastening/cutting assembly including an anvil and a pusher rotatably mounted on the fastening and cutting assembly;
   b) a handle operatively connected to the fastening/cutting assembly for rotating the pusher towards the anvil; and
   c) a staple cartridge associated with the pusher including a plurality of staples, a first staple forming driver aligned with one of the staples, slidably mounted in the staple cartridge and coupled to the pusher, and a knife rotatably mounted on the staple cartridge and coupled to the pusher, wherein upon rotation of the pusher towards the anvil, the knife forms an incision in the body tissue and the first staple forming driver forms a staple in the body tissue adjacent the incision.

11. An instrument as recited in claim 10, further comprising a second staple forming driver, each staple forming driver defining an aperture,
   wherein the pusher has two prongs coupling to the apertures of the staple forming drivers and a third prong coupling to a notch defined by the knife, and
   wherein the plurality of staples form two rows, one staple of each row being aligned with the first and second staple forming drivers, respectively, such that as the pusher rotates towards the anvil, a staple is formed in the body tissue on opposing sides of the incision.

12. An instrument as recited in claim 11, wherein the anvil defines an elongated slot for receiving the knife and staple forming cups on opposing sides of the elongated slot.

13. An instrument as recited in claim 11, wherein the two prongs are chamfered to repeatedly and assuredly engage the apertures.

14. An instrument as recited in claim 10, further comprising a housing rotatably mounted on the anvil and partially surrounding the pusher for receiving the staple cartridge.

15. An instrument as recited in claim 10, wherein the housing and pusher independently rotate and as the housing rotates toward the anvil, the body tissue is secured therebetween.

16. An instrument for stapling and cutting body tissue comprising:
   a) a clamping jaw including:
      i) an anvil defining an elongated slot and staple forming cups on opposing sides of the elongated slot;
      ii) a housing rotatably mounted on the anvil; and
      iii) a pusher rotatably mounted within the housing;
   b) a handle portion connected to the clamping jaw and including means for actuating the clamping jaw from an open position to an intermediate position by rotating the housing towards the clamping jaw to capture the body tissue therebetween, and for actuating the clamping jaw from the intermediate position to a closed position by rotating the pusher towards the anvil; and
   c) a staple cartridge disposed in the housing and including:
      i) a staple track for retaining two rows of staples, each row being laterally spaced from the elongated slot;
      ii) two staple forming drivers, each staple forming driver aligned with the forming cups, the drivers being slidably mounted in the staple cartridge and coupled to the pusher such that each staple forming driver forces a single staple from each row into the forming cups and, in turn, staples the body tissue as the pusher rotates from the intermediate to the closed position; and
      iii) a knife rotatably mounted on the staple cartridge and coupled to the pusher such that the knife passes into the elongated slot and, in turn, cuts the body tissue as the pusher rotates from the intermediate to the closed position.

17. An instrument as recited in claim 16, further comprising an elongated body portion extending between the clamping jaw and handle portion, the elongated body portion having means for articulating the clamping jaw.

18. An instrument as recited in claim 17, wherein the means for articulating is a steering knuckle assembly connected by a cable to a manual adjustment wheel mounted on the handle portion.

19. An instrument as recited in claim 16, wherein the means for actuating is: a firing linkage assembly connected to a trigger in the handle portion; and a cable assembly extending from the firing linkage assembly to the clamping jaw.

20. An instrument as recited in claim 16, further comprising a spring biased between the staples and a staple spring retainer for advancing the staples.

21. A surgical instrument for stapling and cutting body tissue comprising:
   a) a handle assembly including an actuation handle mounted for pivotal movement relative to a stationary handle;
   b) an elongated tubular body portion extending distally from the handle portion and defining a longitudinal axis;
   c) a fastening assembly operatively associated with a distal end portion of the elongated tubular body portion and including:
      i) an elongated anvil portion having laterally opposed staple forming surfaces at a distal end thereof;
      ii) an elongated housing portion mounted for pivotal movement relative to the anvil portion between an open position and a closed position;
      iii) a cartridge supported within the housing portion and carrying two laterally spaced apart longitudinally extending rows of staples, each row of staples having a staple pusher movably mounted at a distal end thereof for urging staples from the cartridge, the cartridge further carrying a cutting knife positioned between the laterally spaced apart rows of staples and mounted for pivotal movement about an axis extending at an angle to the staple rows; and
      iv) a forked lever supported within the housing portion and mounted for pivotal movement relative to the cartridge, the lever having means for operatively engaging the staple pushers and means for operatively engaging the cutting knife; and
   d) first and second actuation cables extending through the body portion between the handle assembly and the fastening assembly, wherein the first actuation cable is operatively connected to the housing portion of the fastening assembly and the second actuation cable is operatively connected to the forked lever of the fastening assembly, and wherein pivotal movement of the actuation handle relative to the stationary handle through a first distance causes the first actuation cable to move the housing portion from the open position spaced from the anvil portion to the closed position approximated with the anvil portion, and pivotal movement of the actuation handle through a second distance causes the second actuation cable to pivot the forked lever into the cartridge, whereby the staple pushers drive respective staples from the cartridge to be formed against the staple forming surfaces of the anvil portion, while the cutting blade pivots about its axis in a path running between the staples driven from the cartridge.

22. A surgical instrument as recited in claim 21, wherein the fastening assembly is mounted for movement relative to the body portion about an axis extending transverse to the longitudinal axis of the body portion.

23. A surgical instrument as recited in claim 22, further comprising means operatively associated with the handle assembly for selectively moving the fastening assembly through an arc relative to the body portion.

24. A surgical instrument as recited in claim 21, further comprising means for normally biasing the housing portion into the open position.

25. A surgical instrument as recited in claim 21, further comprising means for biasing the staples in a distal direction within staple supporting channels formed in the cartridge.

26. A surgical instrument as recited in claim 21, further comprising means for selectively moving the body portion about the longitudinal axis thereof relative to the handle assembly.

27. A surgical instrument as recited in claim 21, wherein the first and second actuation cables are operatively connected to a linkage mechanism disposed within the handle assembly and operated by the actuation handle.

* * * * *